United States Patent
Saito et al.

(10) Patent No.: US 11,021,428 B2
(45) Date of Patent: Jun. 1, 2021

(54) METHOD FOR PRODUCING CIS,CIS-1,2,4-CYCLOHEXANE TRICARBOXYLIC ACID CRYSTAL

(71) Applicant: MITSUBISHI GAS CHEMICAL COMPANY, INC., Chiyoda-ku (JP)

(72) Inventors: Shinya Saito, Okayama (JP); Tatsuyuki Kumano, Okayama (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days.

(21) Appl. No.: 16/496,593

(22) PCT Filed: Mar. 19, 2018

(86) PCT No.: PCT/JP2018/010784
§ 371 (c)(1),
(2) Date: Sep. 23, 2019

(87) PCT Pub. No.: WO2018/180696
PCT Pub. Date: Oct. 4, 2018

(65) Prior Publication Data
US 2020/0317596 A1  Oct. 8, 2020

(30) Foreign Application Priority Data
Mar. 29, 2017 (JP) .............................. JP2017-065918

(51) Int. Cl.
C07C 51/43 (2006.01)
C07C 61/08 (2006.01)
(52) U.S. Cl.
CPC .......... C07C 51/43 (2013.01); C07B 2200/13 (2013.01); C07C 61/08 (2013.01)
(58) Field of Classification Search
CPC ......... C07C 51/43; C07C 61/08; C07C 61/09; C07B 2200/13
See application file for complete search history.

(56) References Cited

U.S. PATENT DOCUMENTS 5,412,108 A * 5/1995 Fisher ................. C07C 51/36
549/245

FOREIGN PATENT DOCUMENTS

JP  2009 057385   *  3/2009
JP  2009-57385 A     3/2009
JP  2013-56856 A     3/2013

OTHER PUBLICATIONS

JP2009 057385 translation (Year: 2009).*
Mettler Toledo (14 pages, published Jul. 2016) (Year: 2016).*
International Search Report dated Apr. 24, 2018 in PCT/JP2018/010784 filed on Mar. 19, 2018.
Isoda, S. et al., "Medicinal Chemical Studies on Antiplasmin Drugs. VIII.[1)] 4-Aminomethylcyclohexanecarboxylic Acid Derivatives having a Carboxyl or Carboxymethyl Group at $C_2$," Chemical & Pharmaceutical Bulletin, vol. 28, No. 8, pp. 2337-2346, 1980.
Omichi, Y. et al., Yuji, et al., "Optical Resolution of DL-Mandelic Acid by Preferential Crystallization Procedure," Journal of the Chemical Society of Japan, No. 8, pp. 1092-1096, 1979 (with English abstract).
Nohira, H., "Optical Resolution of Organic Compounds by Means of Crystallization and Their Applications," Journal of Synthetic Organic Chemistry, vol. 50, No. 1, pp. 14-23, 1992 (with English abstract).
Okamoto, Y. et al., "Resolution of Enantiomers," Chemical education, vol. 43, No. 11, pp. 695-699, The Chemical Society of Japan, 1995.

* cited by examiner

*Primary Examiner* — Yevgeny Valenrod
*Assistant Examiner* — Blaine G Doletski
(74) *Attorney, Agent, or Firm* — Oblon, McClelland, Maier & Neustadt, L.L.P.

(57) ABSTRACT

An object of the present invention is to provide a method for producing cis,cis-1,2,4-cyclohexanetricarboxylic acid crystals, from which high purity cis,cis-1,2,4-cyclohexanetricarboxylic acid crystals are obtained. The method for producing cis,cis-1,2,4-cyclohexanetricarboxylic acid crystals of the present invention comprises the following steps: Step 1: measuring a mass ratio (cis/trans ratio) of cis,cis-1,2,4-cyclohexanetricarboxylic acid to trans,trans-1,2,4-cyclohexanetricarboxylic acid in an aqueous starting material solution comprising the cis,cis-1,2,4-cyclohexanetricarboxylic acid to give an aqueous starting material solution for crystal precipitation having a cis/trans ratio of 10 or more; and Step 2: subjecting the aqueous starting material solution for crystal precipitation obtained in step 1 to crystal precipitation.

20 Claims, No Drawings

METHOD FOR PRODUCING CIS,CIS-1,2,4-CYCLOHEXANE TRICARBOXYLIC ACID CRYSTAL

TECHNICAL FIELD

The present invention relates to a method for producing cis,cis-1,2,4-cyclohexanetricarboxylic acid crystals.

BACKGROUND ART cis,cis-1,2,4-Cyclohexanetricarboxylic anhydride is used as a starting material of resins for optical material and electronic material applications and, for example, is increasingly used as a starting material of solder resists and polyamideimide resins.

As the starting material of the resins, cis,cis-1,2,4-cyclohexanetricarboxylic anhydride has free carboxy groups and thus can impart acidic characteristics derived therefrom and can impart heat resistance and weather resistance derived from the aliphatic ring.

cis,cis-1,2,4-Cyclohexanetricarboxylic anhydride is obtained by subjecting cis,cis-1,2,4-cyclohexanetricarboxylic acid to a dehydration reaction in acetic acid and acetic anhydride.

An example of a common method for producing 1,2,4-cyclohexanetricarboxylic anhydride is a method involving subjecting trimellitic acid to nuclear hydrogenation to give 1,2,4-cyclohexanetricarboxylic acid, purifying 1,2,4-cyclohexanetricarboxylic acid by crystal precipitation, and then carrying out a dehydration reaction.

As for the steps of subjecting trimellitic acid to nuclear hydrogenation to give 1,2,4-cyclohexanetricarboxylic acid and purifying the resulting 1,2,4-cyclohexanetricarboxylic acid by crystal precipitation, for example, PTL1 discloses that trimellitic acid is subjected to nuclear hydrogenation in a mixed solvent of water and tetrahydrofuran (THF) using a transition metal catalyst, the resulting solution is concentrated and dried, and thereby yellowish white crystals are obtained. Moreover, according to PTL1, the crystals are dissolved again in a mixed solution of THF and acetonitrile, and the solution is then concentrated and cooled for crystal precipitation to give cis,cis-1,2,4-cyclohexanetricarboxylic acid.

PTL2 discloses a method for producing 1,2,4-cyclohexanetricarboxylic acid, wherein the step of subjecting trimellitic acid to nuclear hydrogenation and the step of crystal precipitation are consistently carried out in water.

CITATION LIST

Patent Literature

PTL1: U.S. Pat. No. 5,412,108 B
PTL2: JP 2009-57385 A

SUMMARY OF INVENTION

Technical Problem

In the method described in PTL1, THF used as a solvent produces an explosive peroxide when exposed to air or oxygen, and is thus not suitably used in an industrial process. Also, in PTL1, when the method progresses from the nuclear hydrogenation step to the crystal precipitation step, a solvent replacement from a nuclear hydrogenation reaction solvent to a crystal precipitation solvent needs to be carried out, which increases the number of processes and is thus not preferable as an industrial process.

Moreover, PTL1 is problematic in terms of being inefficient because the mass ratio of (the solvent/the charged starting material) during the hydrogenation reaction and after concentration on crystal precipitation is high, and a large amount of solvent is required.

The method of PTL2 is advantageous as an industrial process. Because, in PTL2, water is used as a solvent in place of THF and acetonitrile used in PTL1, the solvent replacement is not required, and thus the method of PTL2 has fewer procedures than the method described in PTL1. Also, the mass ratio of (the solvent/the charged starting material) during the hydrogenation reaction and the mass ratio of (the solvent/the charged starting material) after concentration on crystal precipitation are both lower than those of PTL1. Thus, the amount of the solvent used is small, and the method of PTL2 is efficient.

However, obtaining high purity cis,cis-1,2,4-cyclohexanetricarboxylic acid crystals from the nuclear hydrogenation reaction solution of trimellitic acid is not taken into consideration.

An object of the present invention is to provide a method for producing cis,cis-1,2,4-cyclohexanetricarboxylic acid crystals, from which high purity cis,cis-1,2,4-cyclohexanetricarboxylic acid crystals are obtained.

Solution to Problem

As a result of having conducted diligent research to solve the above problem, the present inventors found that configuring the mass ratio of cis,cis-1,2,4-cyclohexanetricarboxylic acid to trans,trans-1,2,4-cyclohexanetetracarboxylic acid in an aqueous starting material solution for crystal precipitation subjected to a crystal precipitation step to be within a specific range improves the purity of the resulting cis,cis-1,2,4-cyclohexanetetracarboxylic acid crystals, and accomplished the present invention. The present invention provides [1] to [7] below.

[1] A method for producing cis,cis-1,2,4-cyclohexanetricarboxylic acid crystals, comprising the following steps:

Step 1: measuring a mass ratio (cis/trans ratio) of cis,cis-1,2,4-cyclohexanetricarboxylic acid to trans,trans-1,2,4-cyclohexanetricarboxylic acid in an aqueous starting material solution comprising the cis,cis-1,2,4-cyclohexanetricarboxylic acid to give an aqueous starting material solution for crystal precipitation having a cis/trans ratio of 10 or more (preferably 15 or more, more preferably 20 or more, and even more preferably 35 or more); and Step 2: subjecting the aqueous starting material solution for crystal precipitation obtained in step 1 to crystal precipitation.

[2] The method according to [1], wherein in step 2, the aqueous starting material solution for crystal precipitation is concentrated, and a mass ratio of a solvent to a solute of the aqueous starting material solution for crystal precipitation after being concentrated is 0.1 to 5 (preferably 0.3 to 3, more preferably 0.5 to 1.5, and even more preferably 0.8 to 1.3).

[3] The method according to [1] or [2], wherein the cis/trans ratio is 40 or more (preferably 45 or more).

[4] The method according to any one of [1] to [3], wherein the resulting cis,cis-1,2,4-cyclohexanetricarboxylic acid crystals have a purity of 90% by mass or more (preferably 95% by mass or more, more preferably 98% by mass or more, and even more preferably 99% by mass or more).

[5] The p method according to any one of [1] to [4], wherein a recovery rate of cis,cis-1,2,4-cyclohexanetricarboxylic acid in step 2 is 60% by mass or more (preferably 65% by mass or more and more preferably 70% by mass or more).

[6] The method according to any one of [1] to [5], wherein seed crystals are added in step 2.

[7] The method according to [6], wherein the seed crystals are added in an amount of 0.01 to 40% by mass (preferably 0.1 to 30% by mass, more preferably 0.5 to 25% by mass, and even more preferably 1 to 20% by mass) based on cis,cis-1,2,4-cyclohexanetricarboxylic acid contained in the aqueous starting material solution for crystal precipitation.

[8] The method according to [6] or [7], wherein a temperature of the aqueous starting material solution for crystal precipitation when the seed crystals are added is 1 to 60° C. (preferably 5 to 55° C. and more preferably 10 to 50° C.).

Advantageous Effects of Invention

The present invention can provide a method for producing cis,cis-1,2,4-cyclohexanetricarboxylic acid crystals, from which high purity cis,cis-1,2,4-cyclohexanetricarboxylic acid crystals are obtained.

DESCRIPTION OF EMBODIMENTS

Below, the present invention will be described in reference to embodiments. In the following description, "A to B" indicating a numerical range denotes "A or more and B or less" (in the case of A<B) or "A or less and B or more" (in the case of A>B). That is, "A to B" denotes a numerical range including end points A and B.

Also, part by mass and % by mass are synonymous with part by weight and % by weight, respectively.

The method for producing cis,cis-1,2,4-cyclohexanetricarboxylic acid crystals of the present invention comprises the following steps:

Step 1: measuring a mass ratio (cis/trans ratio) of cis,cis-1,2,4-cyclohexanetricarboxylic acid to trans,trans-1,2,4-cyclohexanetricarboxylic acid in an aqueous starting material solution comprising the cis,cis-1,2,4-cyclohexanetricarboxylic acid to give an aqueous starting material solution for crystal precipitation having a cis/trans ratio of 10 or more; and Step 2: subjecting the aqueous starting material solution for crystal precipitation obtained in step 1 to crystal precipitation.

As described above, cis,cis-1,2,4-cyclohexanetricarboxylic anhydride (hereinafter also referred to as cis-H-TMAn) is an important material of polyamideimide resins and solder resists. cis,cis-1,2,4-Cyclohexanetricarboxylic anhydride (cis-H-TMAn) is generally produced by a method for obtaining cis,cis-1,2,4-cyclohexanetricarboxylic anhydride (cis-H-TMAn) involving subjecting the aromatic ring of trimellitic acid (TMA) to nuclear hydrogenation to give cis,cis-1,2,4-cyclohexanetricarboxylic acid (cis-H-TMA), and then subjecting cis-H-TMA to a dehydration reaction.

Here, in the hydrogenation reaction of the aromatic ring of trimellitic acid (TMA), structural isomers such as trans,trans-1,2,4-cyclohexanetricarboxylic acid (trans-H-TMA) and a by-product in which one carboxy group of 1,2,4-cyclohexanetricarboxylic acid is replaced with a methyl group (4-methylcyclohexane-1,2-dicarboxylic anhydride: Me-HHPA) are produced other than the intended cis,cis-1,2,4-cyclohexanetricarboxylic acid. Accordingly, in order to obtain high purity cis-H-TMA, it is necessary that an aqueous starting material solution containing cis,cis-1,2,4-cyclohexanetricarboxylic acid obtained after the hydrogenation of trimellitic acid (TMA) (hereinafter referred to as a TMA nuclear hydrogenation reaction solution) is subjected to crystal precipitation to selectively obtain cis-H-TMA.

This time, the inventors found that when the aqueous starting material solution containing cis,cis-1,2,4-cyclohexanetricarboxylic acid obtained after the nuclear hydrogenation reaction of trimellitic acid is subjected to a crystal precipitation step, measuring the mass ratio (hereinafter referred to as the cis/trans ratio) of the cis,cis-1,2,4-cyclohexanetricarboxylic acid isomer (cis-H-TMA) represented by formula (1) below to the trans,trans-1,2,4-cyclohexanetricarboxylic acid isomer (trans-H-TMA) represented by formula (2) below in the aqueous starting material solution to give an aqueous starting material solution for crystal precipitation having a cis/trans ratio within a specific range and subjecting this to crystal precipitation yield high purity cis-H-TMA crystals.

In the present invention, the purity of the resulting cis-H-TMA crystals is higher than the purity of cis-H-TMA in the aqueous starting material solution for crystal precipitation. Although the details of the reason why such an effect is obtained are not clear, part of the reason is inferred as follows.

That is, it is conjectured that, at the time of crystal precipitation of cis-H-TMA crystals, the use of an aqueous starting material solution for crystal precipitation having a specific cis/trans ratio or higher enables cis-H-TMA crystals having an extremely high purity to be obtained without allowing trans-H-TMA to be concomitantly present in the crystals.

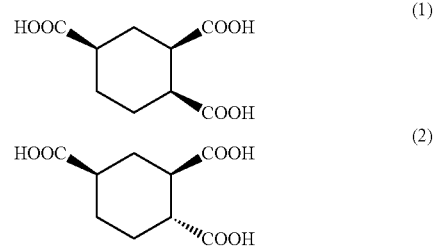

The present invention will be described in detail below.
[Step 1]

In the method for producing cis-H-TMA crystals of the present invention, step 1 is the step of measuring the cis/trans ratio in an aqueous starting material solution comprising cis-H-TMA to give an aqueous starting material solution for crystal precipitation having a cis/trans ratio of 10 or more.

<Aqueous Starting Material Solution>

In the present invention, the aqueous starting material solution is not particularly limited as long as it is an aqueous solution containing cis-H-TMA, and is preferably a nuclear hydrogenation reaction solution of trimellitic acid, which will be described below.

The aqueous starting material solution contains water as a solvent. The water content in the solvent is 50% by mass or more, preferably 60% by mass or more, more preferably 80% by mass or more, and even more preferably 90% by mass or more, and furthermore preferably the solvent is solely composed of water. Water is preferably ion-exchanged water or distilled water. In the case where the resulting cis-H-TMA crystals are used in the electric and electronic fields, water in which the content of metal components such as sodium, potassium, calcium, magnesium, and iron is as small as possible is preferably used.

The aqueous starting material solution may further contain, in addition to water as a solvent, other solvents as long as such solvents are miscible with water, and specific examples include acetic acid, propionic acid, dimethyl ether, methyl ethyl ether, methyl acetate, ethyl acetate, propyl acetate, tetrahydrofuran, acetone, methyl ethyl ketone, ethylene glycol dimethyl ether, diethylene glycol dimethyl ether, and triethylene glycol dimethyl ether.

An example of a method for subjecting trimellitic acid to a nuclear hydrogenation reaction is a method involving hydrogen (hydrogen molecules) as a hydrogen source and a noble metal catalyst as a catalyst.

More specific examples include a method in which trimellitic acid is hydrogenated at a hydrogen partial pressure of 1 MPa or more in the presence of a catalyst containing a noble metal composed of rhodium or palladium or both in a proportion of 0.5 to 10 parts by mass per 100 parts by mass of trimellitic acid as described in JP 2003-286422 A; and a method in which a supported catalyst containing rhodium supported on a carbon carrier and a supported catalyst containing palladium supported on a carbon carrier are used as catalysts, and the aromatic ring of an aromatic polycarboxylic acid is hydrogenated at a specific reaction hydrogen partial pressure at a specific reaction temperature in the presence of the catalysts in specific amounts thereof as described in WO 2010/010869.

Another example is a method in which a catalyst containing a transition metal supported on a carbon carrier having a specific surface area is used, and TMA is hydrogenated by hydrogen molecules under pressure and heat as described in PTL1.

The cis-H-TMA content in the product of the nuclear hydrogenation reaction of trimellitic acid varies depending on the catalyst used, the reaction temperature, and the like. In the present invention, it is preferable to select nuclear hydrogenation reaction conditions having a large cis-H-TMA content and an excellent yield.

The trimellitic acid as a starting material is not particularly limited. A commercially available product may be used, or a commercially available trimellitic anhydride may be used after hydrolysis.

In the present invention, the reaction solution of the nuclear hydrogenation reaction of trimellitic acid is preferably used as an aqueous starting material solution after removing the catalyst by filtration. During separation by filtration, the catalyst is preferably separated by filtration at a temperature similar to the reaction temperature.

<Aqueous Starting Material Solution for Crystal Precipitation>

In step 1, the mass ratio (cis/trans ratio) of cis-H-TMA to trans-H-TMA in the aqueous starting material solution containing cis-H-TMA obtained as described above is measured to give an aqueous starting material solution for crystal precipitation having a cis/trans ratio of 10 or more.

Here, the method for measuring the cis/trans ratio in the aqueous starting material solution is not particularly limited. An example is a method in which cis-H-TMA and trans-H-TMA in the aqueous starting material solution is esterified and then analyzed by gas chromatography, and, specifically, the cis/trans ratio is measured by the method described in the Examples.

In the present invention, the cis/trans ratio of the aqueous starting material solution for crystal precipitation is 10 or more. When the cis/trans ratio of the aqueous starting material solution for crystal precipitation is 10 or more, high purity cis-H-TMA crystals are obtained.

The cis/trans ratio of the aqueous starting material solution for crystal precipitation is preferably 15 or more, more preferably 20 or more, even more preferably 35 or more, further preferably 40 or more, and furthermore preferably 45 or more. A cis/trans ratio of the aqueous starting material solution for crystal precipitation of 40 or more results in a particularly increased recovery rate of cis-H-TMA crystals and is thus preferable.

The upper limit of the cis/trans ratio of the aqueous starting material solution for crystal precipitation is not particularly limited, and is preferably 1000 or less, more preferably 500 or less, even more preferably 80 or less, further preferably 75 or less, and furthermore preferably 70 or less from the viewpoint of the ease of preparing the aqueous starting material solution for crystal precipitation and from the viewpoint that the effect of further increasing the cis/trans ratio is small.

When the measured cis/trans ratio of the aqueous starting material solution is less than 10, the cis/trans ratio of the aqueous starting material solution is preferably configured to be 10 or more by adding cis-H-TMA such that the cis/trans ratio is 10 or more. Also, an aqueous starting material solution having a cis/trans ratio of 10 or more may be mixed with the aqueous starting material solution having cis/trans ratio of less than 10 so as to make a cis/trans ratio of 10 or more, and the method for configuring the cis/trans ratio to be 10 or more is not particularly limited.

Among these, a method involving adding cis-H-TMA is preferable because the cis/trans ratio can be easily improved.

When the measured cis/trans ratio of the aqueous starting material solution is 10 or more, the aqueous starting material solution may be used as-is as the aqueous starting material solution for crystal precipitation. Also, cis-H-TMA may be added to the aqueous starting material solution to further increase the cis/trans ratio.

In the method for producing cis-H-TMA crystals of the present invention, in the case where the aqueous starting material solution is obtained by the hydrogenation reaction of TMA, the cis/trans ratio is not necessary measured every time if it is clear from the reaction condition settings that the cis/trans ratio is 10 or more, and step 2 may be suitably carried out while omitting the measurement of the cis/trans ratio. Such an embodiment is also encompassed within the scope of the present invention.

[Step 2]

In the present invention, step 2 is the step (crystal precipitation step) of subjecting the aqueous starting material solution for crystal precipitation obtained in step 1 to crystal precipitation.

In the crystal precipitation step, it is preferable that the aqueous starting material solution for crystal precipitation is concentrated to prepare a concentrate and, further, the concentrate is cooled to precipitate crystals. It is preferable to add seed crystals before cooling, during cooling, or after cooling the concentrate. These processes will be described in detail below.

<Preparation of Concentrate>

In the present invention, it is preferable that the aqueous starting material solution for crystal precipitation obtained in step 1 is concentrated to prepare a concentrate. The concentration method is not particularly limited, and the aqueous solution is concentrated by removing the solvent. Preferably, the aqueous starting material solution for crystal precipitation is concentrated by heating to distill off the solvent in the aqueous starting material solution for crystal precipitation.

The heating temperature (the temperature of the reaction solution) is not particularly limited, and is preferably 50 to 150° C., more preferably 80 to 140° C., and even more preferably 100 to 130° C.

The concentration is not particularly limited, and may be carried out under atmospheric pressure or reduced pressure. When concentration is carried out (the solvent is distilled off) under reduced pressure, the pressure is preferably 30 to 450 hPa, more preferably 70 to 300 hPa, and even more preferably 100 to 200 hPa.

At the time of concentrating the aqueous solution, the aqueous solution is preferably concentrated while being stirred from the viewpoint of suppressing temperature distribution in the concentrate and preventing bumping.

The stirring speed when the aqueous solution is concentrated is not particularly limited as long as the solution is sufficiently stirred, and the stirring speed is preferably 50 rpm to 1000 rpm, more preferably 100 rpm to 800 rpm, and even more preferably 200 rpm to 600 rpm.

In the aqueous starting material solution for crystal precipitation after being concentrated (hereinafter also referred to as a "concentrate"), the mass ratio (the solvent/the total H-TMA, hereinafter also referred to as "SR") of the solvent to the total H-TMA (H-TMA as a total of 4 isomers) is preferably 0.1 to 5, more preferably 0.3 to 3, even more preferably 0.5 to 1.5, and further preferably 0.8 to 1.3. An SR within the above range is preferable because the recovery rate in the crystal precipitation step is improved within an industrially practicable range.

<Cooling>

The concentrate having a desired SR is preferably cooled.

When the concentrate is prepared by heating, the cooling rate is preferably 1 to 40° C./h, more preferably 5 to 30° C./h, and even more preferably 10 to 20° C./h from the viewpoint of obtaining high purity cis-H-TMA or from the viewpoint of efficiency and a batch cycle.

The concentrate is preferably cooled to 0 to 40° C., more preferably 3 to 30° C., and even more preferably 5 to 20° C. Cooling to the above temperature is preferable because precipitation of crystals is promoted, and the recovery rate of cis-H-TMA crystals is improved.

The concentrate may be stirred while being cooled.

After being cooled, the concentrate is preferably retained at the cooling temperature for 0.5 to 72 hours, more preferably for 1 to 48 hours, and even more preferably for 1.5 to 24 hours. The concentrate may be stirred while being retained at the cooling temperature. Cooling the concentrate for the above retention time is preferable because precipitation of crystals is promoted, and the recovery rate of cis-H-TMA crystals is improved.

The stirring speed is not particularly limited as long as the liquid is sufficiently stirred during cooling and retaining, and is preferably 50 rpm to 1000 rpm, more preferably 100 rpm to 800 rpm, and even more preferably 200 rpm to 600 rpm.

<Addition of Seed Crystals>

In the present invention, seed crystals are preferably added before cooling, during cooling, or after cooling. The seed crystals are preferably added during cooling, and the temperature of the concentrate when the seed crystals are added is preferably 1 to 60° C., more preferably 5 to 55° C., and even more preferably 10 to 50° C.

The seed crystals are preferably added in an amount of 0.01 to 40% by mass, more preferably 0.1 to 30% by mass, even more preferably 0.5 to 25% by mass, and further preferably 1 to 20% by mass, based on the total H-TMA contained in the aqueous starting material solution for crystal precipitation.

The seed crystals to be added may be cis-H-TMA crystals, and a seed crystal slurry may be added.

The seed crystal slurry is a solution which includes even small amounts of cis-H-TMA crystals at 40° C. The cis-H-TMA concentration in the seed crystal slurry is preferably 1 to 60% by mass, more preferably 5 to 50% by mass, and even more preferably 10 to 45% by mass. Examples of the solvent of the seed crystal slurry are the same as those of the solvent in the aqueous starting material solution. And the same solvent as the solvent of the aqueous starting material solution is preferably used.

As will be described below, the mother liquor after step 2 may be used as a seed crystal slurry as-is, or a seed crystal slurry obtained by further adding cis-H-TMA to the mother liquor may be used.

The recovery rate of cis-H-TMA in step 2 is preferably 60% by mass or more, more preferably 65% by mass or more, and even more preferably 70% by mass or more.

By increasing the cis/trans ratio in the aqueous starting material solution for crystal precipitation, the recovery rate of cis-H-TMA in step 2 can be improved, and as described above, the cis/trans ratio is particularly preferably 40 or more from the viewpoint of improving the recovery rate of cis-H-TMA in step 2.

The recovery rate of cis-H-TMA in step 2 is measured by the method described in the Examples.

Step of Isolating cis,cis-1,2,4-cyclohexanetricarboxylic acid

In the present invention, the method preferably has the step of isolating cis-H-TMA crystals (hereinafter also simply referred to as an "isolation step") subsequent to step 2.

By separating the crystals (solids) precipitated in step 2 by filtration and, further, drying the solids that have been separated by filtration, cis-H-TMA crystals can be isolated.

The mother liquor from which the crystals have been separated may be used as a mother liquor for a seed crystal slurry. Whether the mother liquor should be used as a mother liquor for a seed crystal slurry or not is determined according to the extent of impurity buildup in the system.

cis,cis-1,2,4-Cyclohexanetetracarboxylic acid crystals

The purity of cis,cis-1,2,4-cyclohexanetricarboxylic acid crystals obtained by the production method of the present invention is higher than the purity of cis-H-TMA in the aqueous starting material for crystal precipitation.

The purity of the resulting cis-H-TMA crystals is preferably 90% by mass or more, more preferably 95% by mass or more, even more preferably 98% by mass or more, and further preferably 99% by mass or more. The purity of cis-H-TMA is preferably high, and the upper limit is 100% by mass.

The purity of cis-H-TMA crystals is measured by the method described in the Examples.

The cis-H-TMA crystals obtained by the production method of the present invention have a high purity, moreover, the recovery rate in step 2 (crystal precipitation step) in the production method of the present invention is high, and therefore the production method of the present invention is industrially advantageous. Also, the resulting cis-H-TMA crystals can be converted to cis,cis-1,2,4-cyclohexanetetracarboxylic anhydride (cis-H-TMAn) by a subsequent dehydration reaction. cis-H-TMAn is useful as a starting material of polyamideimide resins and a starting material of solder resists.

As described above, the production method of the present invention capable of providing high purity cis-H-TMA crystals at a high recovery rate is extremely industrially advantageous.

EXAMPLES

The present invention will be described in more detail by way of Examples and Comparative Examples below, but the present invention is not limited to these Examples.

[Measurement Method]

(1) Measurement of H-TMA Purity (Trimethyl Phosphate Method)

The H-TMA purity in the resulting crystals was measured as follows.

Specifically, an aqueous solution containing the resulting crystals (concentration of 5 to 30% by mass) was prepared, 0.60 g of the solution was placed in a test tube, then 3.0 g of triethylammonium chloride (manufactured by Wako Pure Chemical Industries, Ltd.) and 10 ml of trimethyl phosphate (manufactured by Kishida Chemical Co., Ltd.) were added, and the mixture was heated in a block heater at 180° C. for 90 minutes to carry out an esterification treatment. Thereafter, 0.10 g of triphenylmethane (manufactured by Tokyo Chemical Industry Co., Ltd.) was added as an internal standard, the mixture was completely dissolved in 9 ml of chloroform, ion-exchanged water was further added to carry out a liquid separation treatment, and the resulting chloroform solution was subjected to a gas chromatography analysis. The H-TMA purity was calculated by the internal standard method using triphenylmethane as an internal standard. Also, the H-TMA purity in the starting material solution (concentration of 5 to 30% by mass) was calculated by the internal standard method in the same manner as the method for calculating the H-TMA purity in the crystals.

(Gas Chromatography Analysis Conditions)

Gas chromatography analyzer: 6890N (manufactured by Agilent Technologies, Inc.)

Capillary column: DB-1 (manufactured by Agilent Technologies, Inc.)

Injection temperature: 300° C.

Detection temperature: 290° C.

Initial column temperature, retention time: 160° C., 20 min

Heating rate: 10° C./min

Final column temperature, retention time: 280° C., 15 min

Carrier gas: Helium

Carrier gas pressure: 33.1 kPa

Detector: FID (2) Analysis of Selectivity Between Cis-H-TMA Form and Trans-H-TMA Form of Cyclohexanetricarboxylic Acid

[Pretreatment]

<Esterification Conditions ($BF_3$.MeOH Method)>

First, 0.60 g of an aqueous starting material solution containing 1,2,4-cyclohexanetricarboxylic acid was placed in a test tube, 10 ml of a boron trifluoride methanol solvent (manufactured by Tokyo Chemical Industry Co., Ltd.) was added, and the mixture was heated for 6 minutes in a block heater at 150° C. to carry out an esterification treatment. After the reaction, 3 ml of chloroform was added, a liquid separation treatment was carried out in the order of water, a 0.5 N aqueous sodium carbonate solution, and water, and the resulting chloroform solution was subjected to a gas chromatography analysis. The selectivity (mass ratio) between cis-H-TMA and trans-H-TMA was calculated according to area percentage.

[Gas Chromatography Analysis Conditions]

The gas chromatography analysis conditions were the same as those in (1) Measurement of H-TMA purity above.

Production Example 1: Preparation of H-TMA Having High Cis Form Purity

First, 327 g of trimellitic anhydride (manufactured by Flint Hills Resources, LLC) and 2174 g of ion-exchanged water were added to a 5 L SUS31GL autoclave equipped with a stirrer, a thermocouple thermometer casing pipe, a pressure gauge, two gas lines (inner diameter of 3 mm), and a vent line, heated at 90° C. for 30 minutes to carry out hydrolysis, and then charged into a reaction vessel.

Subsequently, a 5% by mass palladium-carbon supported catalyst PE type (manufactured by N.E. Chemcat Corporation, obtained by drying a product wetted with water under 110° C. and 8-hour conditions) in an amount of 78.5 g (1.2 parts by mass in terms of palladium metal based on 100 parts by mass of trimellitic acid (hereinafter also referred to as "TMA")) and a 5% by mass rhodium-carbon supported catalyst (manufactured by N.E. Chemcat Corporation, obtained by drying a product wetted with water under 110° C. and 8-hour conditions) in an amount of 33.6 g (0.5 parts by mass in terms of rhodium metal based on 100 parts by mass of TMA) were charged into the reaction vessel. The Pd:Rh ratio (mass ratio) of the catalyst was 7:3.

While stirring the contents, the system was purged with 2.0 MPa of nitrogen gas twice, and then the system was purged with 2.0 MPa of hydrogen gas once. At this time, the stirring speed was 700 rpm. The pressure was raised to 3.0 MPa by hydrogen gas, and the reaction was started at a solution temperature of 30° C. The pressure was lowered 2 hours after the beginning of the reaction.

After the pressure was lowered, the reaction solution was discharged from the bottom of the autoclave by nitrogen pressure. From this filtrate (crude reaction product) reaction solution, the catalyst was separated by filtration using ADVANTEC 5B filter paper (JIS P 3801) to obtain a transparent nuclear hydrogenation reaction solution (aqueous starting material solution).

The nuclear hydrogenation reaction solution was charged into a 4 L jacketed SUS316L autoclave equipped with a stirrer, two thermocouple thermometer casing pipes, two heat exchangers, a starting material feeding line, and an inspection hole to start concentration at a stirring speed of 200 rpm, and concentrated until the total H-TMA concentration reached 45.5% by mass.

After the temperature was lowered to 20° C., the slurry was discharged to carry out solid-liquid separation. The resulting crystals were dried at 110° C. for 8 hours in a drier to obtain crystals 1. The H-TMA purity (the purity of 1,2,4-cyclohexanetricarboxylic acid as a total of 4 isomers) in the crystals 1 was 97.0% by mass. As for the isomer proportions in the crystals, the trans form was 0.1% by mass, and the cis form was 99.8% by mass. The cis-H-TMA purity in the crystals was 97.0×0.998=96.8% by mass.

Production Example 2: Preparation of H-TMA Having High Trans Form Purity 1,2,4-Cyclohexanetricarboxylic acid was charged into a four-neck flask equipped with a thermometer, a stirrer, a condenser, and a temperature controller, and thermally melted at 250° C. for 3 hours in a nitrogen gas stream to obtain 1,2,4-cyclohexanetricarboxylic acid 1,2-anhydride in the form of a pale yellow transparent liquid. The dehydration rate in terms of the 1,2,4-cyclohexanetricarboxylic acid as a starting material was 95%.

In the liquid anhydride, trans,trans-1,2,4-cyclohexanetricarboxylic acid 1,2-anhydride was 56% by mass, and cis,cis-1,2,4-cyclohexanetricarboxylic acid 1,2-anhydride was 44% by mass.

Then, 1000 g of the above liquid cyclohexanetricarboxylic anhydride and 3000 g of water were added to a 5 L flask, and the mixture was stirred at 80° C. for 1 hour. Thereafter, the reaction system was cooled to 25° C. to precipitate crystals. The crystals were subjected to suction filtration using a Buchner funnel and then vacuum-dried to obtain crystals 2. The H-TMA purity (the purity of 1,2,4-cyclohexanetricarboxylic acid as a total of 4 isomers) in the crystals 2 was 99.3% by mass. As for the proportions of H-TMA isomers in the crystals (the proportions of the respective isomers in H-TMA), the trans form was 97.2% by mass, and the cis form was 2.6% by mass. The trans-H-TMA purity in the crystals was 99.3×0.972=96.5% by mass.

Table 1 below shows details of the crystals 1 obtained in Production Example 1 and the crystals 2 obtained in Production Example 2.

TABLE 1

|  | The crystals 1 (Production Example 1) | The crystals 2 (Production Example 2) |
| --- | --- | --- |
| H-TMA purity (% by mass) | 97.0 | 99.3 |
| cis form isomer proportion (% by mass) | 99.8 | 2.6 |
| trans form isomer proportion (% by mass) | 0.1 | 97.2 |
| cis form purity (% by mass) in crystals | 96.8 | 2.6 |
| trans form purity (% by mass) in crystals | 0.1 | 96.5 |

Example 1

First, 749.5 g of the crystals 1 obtained in Production Example 1, 8.2 g of the crystals 2 obtained in Production Example 2, and 5000 g of pure water were charged into a 4 L jacketed SUS316L autoclave equipped with a stirrer, two thermocouple thermometer casing pipes, two heat exchangers, a starting material feeding line, and an inspection hole, and dissolved.

This solution was regarded as an aqueous starting material solution for crystal precipitation 1. The mass of total H-TMA contained in the aqueous starting material solution for crystal precipitation 1 was 735.2 g (the mass of cis-H-TMA was 725.8 g). The cis/trans ratio of the aqueous starting material solution for crystal precipitation 1 was 84.0.

The aqueous starting material solution for crystal precipitation 1 was thermally concentrated at a stirring speed of 200 rpm, and the solution was concentrated until the concentration was 45.5% by mass (the solvent/total H-TMA mass ratio=1.2 (hereinafter also referred to as SR)). After concentration, 1615.8 g of a concentrate 1 was present in the autoclave, and the temperature of the concentrate was 100° C. The concentration refers to the concentration of the total H-TMA, and is calculated by Concentration (% by mass) =Total H-TMA (mass)/(Solute+Solvent) (mass)×100.

Next, the temperature of the concentrate 1 was lowered at 10° C./h while stirring the concentrate 1 at 576 rpm. When the temperature of the concentrate reached 40.0° C., 147.2 g of seed crystals (142.5 g in terms of cis-H-TMA) provided in advance were added through the inspection hole. Thereafter, the temperature was further lowered to 20° C. at 10° C./h, and stirring was continued at 20° C. for 12 hours.

Thereafter, the slurry was recovered from the bottom of the reaction vessel and subjected to suction filtration for 15 minutes with a Buchner funnel. The crystals were recovered with a spatula, and the resulting crystals were dried in a drier at 110° C. for 8 hours.

The recovered dry mass of the dried cis-H-TMA crystals was 675.3 g, and the recovery rate was 72.6% by mass. The purity of H-TMA in the resulting crystals was 99.6% by mass, the cis-H-TMA selectivity (purity) in H-TMA was 99.5% by mass, and thus the cis-H-TMA purity was 99.6× 0.995=99.1% by mass.

The recovery rate was calculated by the following formula:

Recovery rate (% by mass)={(Mass of cis-H-TMA in resulting crystals)−(Mass of cis-H-TMA in added seed crystals)}/(Mass of cis-H-TMA in starting material)×100

The analysis results of the H-TMA crystals (recovered crystals) obtained in Example 1 are shown in Table 2.

The seed crystals used in Example 1, and Examples 2 to 6 and Comparative Examples 1 and 2 which will be described below, were prepared as follows.

The nuclear hydrogenation reaction and crystal precipitation were carried out in the same manner as in Production Example 1 except that a palladium-carbon supported catalyst PE type (manufactured by N.E. Chemcat Corporation, obtained by drying a product wetted with water under 110° C. and 8-hour conditions) in an amount of 100.9 g (1.5 parts by mass in terms of palladium metal based on 100 parts by mass of TMA) and a 5% by mass rhodium-carbon supported catalyst (manufactured by N.E. Chemcat Corporation, obtained by drying a product wetted with water under 110° C. and 8-hour conditions) in an amount of 11.2 g (0.2 parts by mass in terms of rhodium metal based on 100 parts by mass of TMA) were charged as hydrogenation catalysts for TMA (Pd:Rh (mass ratio) of the catalysts=9:1) and, further, solid-liquid separation and drying were carried out. The cis-H-TMA purity in the resulting crystals was 96.8% by mass, and the resulting crystals were used as seed crystals in the Examples and the Comparative Examples.

Example 2

A solution obtained by dissolving 751.7 g of the crystals 1 obtained in Production Example 1 and 15.5 g of the crystals 2 obtained in Production Example 2 in 5000 g of pure water in the same autoclave as in Example 1 was regarded as an aqueous starting material solution for crystal precipitation 2. The mass of total H-TMA contained in the aqueous starting material solution for crystal precipitation 2 was 744.5 g (the mass of cis-H-TMA was 728.1 g). The cis/trans ratio of the aqueous starting material solution for crystal precipitation 2 was 46.4.

The aqueous starting material solution for crystal precipitation 2 was concentrated at a stirring speed of 200 rpm until the concentration was 45.5% by mass (the solvent/total H-TMA mass ratio=1.2 (hereinafter also referred to as SR)). After concentration, 1636.3 g of a concentrate 2 was present in the autoclave, and the temperature of the concentrate was 100° C.

Next, the temperature of the concentrate 2 was lowered at 10° C./h while stirring the concentrate 2 at 576 rpm. When the temperature of the concentrate reached 40.0° C., 147.2 g of seed crystals (142.5 g in terms of cis-H-TMA) provided in advance were added through the inspection hole. Thereafter, the temperature was further lowered to 20° C. at 10° C./h, and stirring was continued at 20° C. for 12 hours.

Thereafter, the same operation as in Example 1 was carried out.

The recovered dry mass of the dried cis-H-TMA crystals was 669.7 g, and the recovery rate was 71.4% by mass. The purity of H-TMA in the resulting crystals was 99.5% by mass, the cis-H-TMA selectivity (purity) in H-TMA was 99.5% by mass, and thus the cis-H-TMA purity was 99.5×0.995=99.0% by mass.

The analysis results of the H-TMA crystals (recovered crystals) obtained in Example 2 are shown in Table 2.

The seed crystals used in Example 2 were the same as those used in Example 1.

Example 3

A solution obtained by dissolving 741.1 g of the crystals 1 obtained in Production Example 1 and 19.1 g of the crystals 2 obtained in Production Example 2 in 5000 g of pure water in the same manner as in Example 1 was regarded as an aqueous starting material solution for crystal precipitation 3. The mass of total H-TMA contained in this aqueous starting material solution for crystal precipitation was 737.8 g (the mass of cis-H-TMA was 717.9 g). The cis/trans ratio of the aqueous starting material solution for crystal precipitation 3 was 37.5.

Concentration was started at a stirring speed of 200 rpm, and the aqueous starting material solution for crystal precipitation was concentrated until the concentration was 45.5% by mass (the solvent/total H-TMA mass ratio=1.2 (hereinafter also referred to as SR)). After concentration, 1621.5 g of a concentrate 3 was present in the autoclave, and the temperature of the concentrate was 100° C.

Next, the temperature of the concentrate 3 was lowered at 10° C./h while stirring the concentrate 3 at 576 rpm. When the temperature of the concentrate reached 40.0° C., 147.6 g of seed crystals (142.9 g in terms of cis-H-TMA) provided in advance were added through the inspection hole. Thereafter, the temperature was further lowered to 20° C. at 10° C./h, and stirring was continued at 20° C. for 12 hours.

Thereafter, the same operation as in Example 1 was carried out.

The recovered dry mass of the dried cis-H-TMA crystals was 625.3 g, and the recovery rate was 66.0% by mass. The purity of H-TMA in the resulting crystals was 99.4% by mass, the cis-H-TMA selectivity (purity) in H-TMA was 99.2% by mass, and thus the cis-H-TMA purity was 99.4×0.992=98.6% by mass.

The analysis results of the H-TMA crystals (recovered crystals) obtained in Example 3 are shown in Table 2.

The seed crystals used in Example 3 were the same as those used in Example 1.

Example 4

A solution obtained by dissolving 728.5 g of the crystals 1 obtained in Production Example 1 and 36.5 g of the crystals 2 obtained in Production Example 2 in 5000 g of pure water in the same manner as in Example 1 was regarded as an aqueous starting material solution for crystal precipitation 4. The mass of total H-TMA contained in this aqueous starting material solution for crystal precipitation was 742.9 g (the mass of cis-H-TMA was 706.2 g). The cis/trans ratio of the aqueous starting material solution for crystal precipitation 4 was 19.7.

Concentration was started at a stirring speed of 200 rpm, and the aqueous starting material solution for crystal precipitation was concentrated until the concentration was 45.5% by mass (the solvent/total H-TMA mass ratio=1.2 (hereinafter also referred to as SR)). After concentration, 1632.7 g of a concentrate 4 was present in the autoclave, and the temperature of the concentrate was 100° C.

Next, the temperature of the concentrate 4 was lowered at 10° C./h while stirring the concentrate 4 at 576 rpm. When the temperature of the concentrate reached 40.0° C., 148.1 g of seed crystals (143.4 g in terms of cis-H-TMA) provided in advance were added through the inspection hole. Thereafter, the temperature was further lowered to 20° C. at 10° C./h, and stirring was continued at 20° C. for 12 hours.

Thereafter, the same operation as in Example 1 was carried out.

The recovered dry mass of the dried cis-H-TMA crystals was 611.5 g, and the recovery rate was 65.2% by mass. The purity of H-TMA in the resulting crystals was 99.9% by mass, the cis-H-TMA selectivity (purity) in H-TMA was 98.9% by mass, and thus the cis-H-TMA purity was 99.9×0.989=98.8% by mass.

The seed crystals used in Example 4 were the same as those used in Example 1.

Example 5

A solution obtained by dissolving 716.2 g of the crystals 1 obtained in Production Example 1 and 45.2 g of the crystals 2 obtained in Production Example 2 in 5000 g of pure water in the same manner as in Example 1 was regarded as an aqueous starting material solution for crystal precipitation 5. The mass of total H-TMA contained in this aqueous starting material solution for crystal precipitation was 739.6 g (the mass of cis-H-TMA was 694.5 g). The cis/trans ratio of the aqueous starting material solution for crystal precipitation 5 was 15.7.

Concentration was started at a stirring speed of 200 rpm, and the aqueous starting material solution for crystal precipitation was concentrated until the concentration was 45.5% by mass (the solvent/total H-TMA mass ratio=1.2 (hereinafter also referred to as SR)). After concentration, 1625.5 g of a concentrate 5 was present in the autoclave, and the temperature of the concentrate was 100° C.

Next, the temperature of the concentrate 5 was lowered at 10° C./h while stirring the concentrate 5 at 576 rpm. When the temperature of the concentrate reached 40.0° C., 147.6 g of seed crystals (142.9 g in terms of cis-H-TMA) provided in advance were added through the inspection hole. Thereafter, the temperature was further lowered to 20° C. at 10° C./h, and stirring was continued at 20° C. for 12 hours.

Thereafter, the same operation as in Example 1 was carried out.

The recovered dry mass of the dried cis-H-TMA crystals was 661.7 g, and the recovery rate was 68.9% by mass. The purity of H-TMA in the resulting crystals was 98.8% by mass, the cis-H-TMA selectivity (purity) in H-TMA was 95.0% by mass, and thus the cis-H-TMA purity was 98.8×0.950=93.9% by mass.

The seed crystals used in Example 5 were the same as those used in Example 1.

Example 6

A solution obtained by dissolving 699.7 g of the crystals 1 obtained in Production Example 1 and 63.7 g of the crystals 2 obtained in Production Example 2 in 5000 g of pure water in the same manner as in Example 1 was regarded as an aqueous starting material solution for crystal precipitation 6. The mass of total H-TMA contained in this aqueous starting material solution for crystal precipitation was 742.0 g (the mass of cis-H-TMA was 679.0 g). The cis/trans ratio of the aqueous starting material solution for crystal precipitation 6 was 10.9.

Concentration was started at a stirring speed of 200 rpm, and the aqueous starting material solution for crystal precipitation was concentrated until the concentration was 45.5% by mass (the solvent/total H-TMA mass ratio=1.2 (hereinafter also referred to as SR)). After concentration, 1630.8 g of a concentrate 6 was present in the autoclave, and the temperature of the concentrate was 100° C.

Next, the temperature of the concentrate 6 was lowered at 10° C./h while stirring the concentrate 6 at 576 rpm. When the temperature of the concentrate reached 40.0° C., 148.0 g of seed crystals (143.3 g in terms of cis-H-TMA) provided in advance were added through the inspection hole. Thereafter, the temperature was further lowered to 20° C. at 10° C./h, and stirring was continued at 20° C. for 12 hours.

Thereafter, the same operation as in Example 1 was carried out.

The recovered dry mass of the dried cis-H-TMA crystals was 607.7 g, and the recovery rate was 61.5% by mass. The purity of H-TMA in the resulting crystals was 99.0% by mass, the cis-H-TMA selectivity (purity) in H-TMA was 93.2% by mass, and thus the cis-H-TMA purity was 99.0× 0.932=92.3% by mass.

The seed crystals used in Example 6 were the same as those used in Example 1.

Comparative Example 1

A solution obtained by dissolving 619.7 g of the crystals 1 obtained in Production Example 1 and 128.9 g of the crystals 2 obtained in Production Example 2 in 5000 g of pure water in the same manner as in Example 1 was regarded as an aqueous starting material solution for crystal precipitation 7. The mass of total H-TMA contained in this aqueous starting material solution for crystal precipitation was 729.1 g (the mass of cis-H-TMA was 603.2 g). The cis/trans ratio of the aqueous starting material solution for crystal precipitation 7 was 4.8.

Concentration was started at a stirring speed of 200 rpm, and the aqueous starting material solution for crystal precipitation was concentrated until the concentration was 45.5% by mass (the solvent/total H-TMA mass ratio=1.2 (hereinafter also referred to as SR)). After concentration, 1602.4 g of a concentrate 7 was present in the autoclave, and the temperature of the concentrate was 100° C.

Next, the temperature of the concentrate 7 was lowered at 10° C./h while stirring the concentrate 7 at 576 rpm. When the temperature of the concentrate reached 40.0° C., 144.1 g of seed crystals (139.5 g in terms of cis-H-TMA) provided in advance were added through the inspection hole. Thereafter, the temperature was further lowered to 20° C. at 10° C./h, and stirring was continued at 20° C. for 12 hours.

Thereafter, the same operation as in Example 1 was carried out.

The recovered dry mass of the dried cis-H-TMA crystals was 677.1 g, and the recovery rate was 67.7% by mass. The purity of H-TMA in the resulting crystals was 99.2% by mass, the cis-H-TMA selectivity (purity) in H-TMA was 81.6% by mass, and thus the cis-H-TMA purity was 99.2× 0.816=80.9% by mass.

The seed crystals used in Comparative Example 1 were the same as those used in Example 1.

Comparative Example 2

A solution obtained by dissolving 516.3 g of the crystals 1 obtained in Production Example 1 and 210.7 g of the crystals 2 obtained in Production Example 2 in 5000 g of pure water in the same manner as in Example 1 was regarded as an aqueous starting material solution for crystal precipitation 8. The mass of total H-TMA contained in this aqueous starting material solution for crystal precipitation was 710.0 g (the mass of cis-H-TMA was 505.2 g). The cis/trans ratio of aqueous starting material solution for crystal precipitation 8 was 2.5.

Concentration was started at a stirring speed of 200 rpm, and the aqueous starting material solution for crystal precipitation was concentrated until the concentration was 45.5% by mass (the solvent/total H-TMA mass ratio=1.2 (hereinafter also referred to as SR)). After concentration, 1560.4 g of a concentrate 8 was present in the autoclave, and the temperature of the concentrate was 100° C.

Next, the temperature of the concentrate 8 was lowered at 10° C./h while stirring the concentrate 8 at 576 rpm. When the temperature of the concentrate reached 40.0° C., 141.4 g of seed crystals (136.9 g in terms of cis-H-TMA) provided in advance were added through the inspection hole. Thereafter, the temperature was further lowered to 20° C. at 10° C./h, and stirring was continued at 20° C. for 12 hours.

Thereafter, the same operation as in Example 1 was carried out.

The recovered dry mass of the dried cis-H-TMA crystals was 640.1 g, and the recovery rate was 61.0% by mass. The purity of H-TMA in the resulting crystals was 98.1% by mass, the cis-H-TMA selectivity (purity) in H-TMA was 70.9% by mass, and thus the cis-H-TMA purity was 98.1× 0.709=69.6% by mass.

The seed crystals used in Comparative Example 2 were the same as those used in Example 1.

TABLE 2

|  |  | Example | | | | | | Comparative Example | |
| --- | --- | --- | --- | --- | --- | --- | --- | --- | --- |
|  |  | 1 | 2 | 3 | 4 | 5 | 6 | 1 | 2 |
| Starting | The crystals 1 added (g) | 749.5 | 751.7 | 741.1 | 728.5 | 716.2 | 699.7 | 619.7 | 516.3 |
| material | The crystals 2 added (g) | 8.2 | 15.5 | 19.1 | 36.5 | 45.2 | 63.7 | 128.9 | 210.7 |
|  | H-TMA content (g) | 735.2 | 744.5 | 737.8 | 742.9 | 739.6 | 742.0 | 729.1 | 710.0 |
|  | cis form content (g) | 725.8 | 728.1 | 717.9 | 706.2 | 694.5 | 679.0 | 603.2 | 505.2 |
|  | trans form content (g) | 8.6 | 15.7 | 19.2 | 35.9 | 44.3 | 62.2 | 125.0 | 203.9 |
|  | cis/trans ratio | 84.0 | 46.4 | 37.5 | 19.7 | 15.7 | 10.9 | 4.8 | 2.5 |
|  | cis form purity (% by mass) in starting material | 95.8 | 94.9 | 94.4 | 92.3 | 91.2 | 88.9 | 80.6 | 69.5 |

TABLE 2-continued

| | | Example | | | | | | Comparative Example | |
|---|---|---|---|---|---|---|---|---|---|
| | | 1 | 2 | 3 | 4 | 5 | 6 | 1 | 2 |
| Seed crystal | cis-H-TMA (g) in seed crystal | 142.5 | 142.5 | 142.9 | 143.4 | 142.9 | 143.3 | 139.5 | 136.9 |
| Crystal | Dry mass (g) of recovered crystal | 675.3 | 669.7 | 625.3 | 611.5 | 661.7 | 607.7 | 677.1 | 640.1 |
| | cis form purity (% by mass) in H-TMA | 99.5 | 99.5 | 99.2 | 98.9 | 95.0 | 93.2 | 81.6 | 70.9 |
| | H-TMA purity (% by mass) | 99.6 | 99.5 | 99.4 | 99.9 | 98.8 | 99.0 | 99.2 | 98.1 |
| | cis form purity (% by mass) | 99.1 | 99.0 | 98.6 | 98.8 | 93.9 | 92.3 | 80.9 | 69.6 |
| | Recovery rate (% by mass) | 72.6 | 71.4 | 66.0 | 65.2 | 68.9 | 61.5 | 67.7 | 61.0 |

INDUSTRIAL APPLICABILITY

As described above, high purity cis,cis-1,2,4-cyclohexanetricarboxylic acid crystals can be obtained by the production method of the present invention.

cis,cis-Cyclohexanetricarboxylic acid obtained by the present invention has high purity and is thus expected to be used as a starting material of polyamideimides, epoxy resin curing agents, solder resists, and the like.

The invention claimed is:

1. A method for producing one or more cis,cis-1,2,4-cyclohexanetricarboxylic acid crystals, the method comprising:
   selecting and/or adjusting a cis/trans mass ratio of cis,cis-1,2,4-cyclohexanetricarboxylic acid to trans,trans-1,2,4-cyclohexanetricarboxylic acid in an aqueous starting material solution comprising the cis,cis-1,2,4-cyclohexanetricarboxylic acid to obtain a selected aqueous starting material solution for crystal precipitation having a cis/trans ratio of 19.7 or more; and
   subjecting the selected aqueous starting material solution to crystal precipitation, to obtain resulting cis,cis-1,2,4-cyclohexanetricarboxylic acid crystals having a purity of 98.8% by mass or more.

2. The method of claim 1, wherein the subjecting comprises concentrating the selected aqueous starting material solution to obtain a solvent-to-solute mass ratio of the selected aqueous starting material solution in a range of from 0.1 to 5.

3. The method of claim 1, wherein the cis/trans ratio is 40 or more.

4. The method of claim 1, wherein the resulting cis,cis-1,2,4-cyclohexanetricarboxylic acid crystals have a purity of 99.0% by mass or more.

5. The method of claim 1, wherein a recovery rate of cis,cis-1,2,4-cyclohexanetricarboxylic acid in the subjecting is 60% by mass or more, relative to a total 1,2,4-cyclohexanetricarboxylic acid mass.

6. The method of claim 1, wherein the subjecting comprises adding seed crystals to the selected aqueous starting material solution.

7. The method of claim 6, wherein the seed crystals are added in an amount of 0.01 to 40% by mass based on cis,cis-1,2,4-cyclohexanetricarboxylic acid contained in the selected aqueous starting material solution.

8. The method of claim 6, wherein the adding of the seed crystals is carried out at a temperature of the selected aqueous starting material solution in a range of from 1 to 60° C.

9. The method of claim 3, wherein resulting cis,cis-1,2,4-cyclohexanetricarboxylic acid crystals have a purity of 90% by mass or more.

10. The method of claim 3, wherein a recovery rate of cis,cis-1,2,4-cyclohexanetricarboxylic acid in the subjecting is 60% by mass or more, relative to a total 1,2,4-cyclohexanetricarboxylic acid mass.

11. The method of claim 3, wherein the subjecting comprises adding seed crystals to the selected aqueous starting material solution.

12. The method of claim 11, wherein the seed crystals are added in an amount in a range of from 0.01 to 40% by mass based on cis,cis-1,2,4-cyclohexanetricarboxylic acid contained in the selected aqueous starting material solution.

13. The method of claim 11, wherein a temperature of the selected aqueous starting material solution when the seed crystals are added is in a range of from 1 to 60° C.

14. The method of claim 1, wherein the resulting cis,cis-1,2,4-cyclohexanetricarboxylic acid crystals have a purity of 99.1% by mass or more.

15. The method of claim 1, wherein the cis/trans ratio is 20 or more.

16. The method of claim 1, wherein the cis/trans ratio is 35 or more.

17. The method of claim 1, wherein the cis/trans ratio is 45 or more.

18. The method of claim 1, wherein the cis/trans ratio no more than 1000.

19. The method of claim 3, wherein the recovery rate of cis,cis-1,2,4-cyclohexanetricarboxylic acid in the subjecting is 65% by mass or more.

20. The method of claim 3, wherein the recovery rate of cis,cis-1,2,4-cyclohexanetricarboxylic acid in the subjecting is 70% by mass or more.

* * * * *